United States Patent [19]

Rosenberg

[11] Patent Number: 5,007,828
[45] Date of Patent: Apr. 16, 1991

[54] MOLAR CONTROLLING AND POSITIONING ORTHODONTIC APPLIANCE WITH SIMPLIFIED ORIENTATION, PRESSURE AND ADJUSTMENT MECHANISMS

[76] Inventor: Farel Rosenberg, Beverly Hills, Calif.
[21] Appl. No.: 476,734
[22] Filed: Feb. 8, 1990
[51] Int. Cl.⁵ ............................................. A61C 3/00
[52] U.S. Cl. .................................... 433/18; 433/7; 433/17
[58] Field of Search .................. 433/6, 7, 17, 18, 19

[56] References Cited

U.S. PATENT DOCUMENTS

| | | | |
|---|---|---|---|
| 2,318,001 | 5/1943 | Linde | 433/7 |
| 4,571,178 | 2/1986 | Rosenberg | 433/19 |
| 4,573,914 | 3/1986 | Nord | 433/18 |
| 4,713,000 | 12/1987 | Rosenberg | 433/18 |
| 4,723,910 | 2/1988 | Keller | 433/7 |
| 4,897,035 | 1/1990 | Greene | 433/17 |

FOREIGN PATENT DOCUMENTS 2909159  9/1980  Fed. Rep. of Germany .......... 433/6

*Primary Examiner*—Gene Mancene
*Assistant Examiner*—Michael Lynch
*Attorney, Agent, or Firm*—Gilbert Kivenson

[57] ABSTRACT

An improved appliance for producing backward movement of molars or adjacent teeth is disclosed. The appliance can be readily removed, adjusted in length to change applied forces and then easily reinstalled.

2 Claims, 1 Drawing Sheet

MOLAR CONTROLLING AND POSITIONING ORTHODONTIC APPLIANCE WITH SIMPLIFIED ORIENTATION, PRESSURE AND ADJUSTMENT MECHANISMS

BACKGROUND OF THE INVENTION

This invention relates to improvements in My Forward-Backward Molar Controlling and Positioning Dental Appliance, U.S. Pat. No. 4,571,178 and my Molar Controlling and Positioning Orthodontic Appliance Adjustable in Three Planes, U.S. Pat. No. 4,713,000. The appliance described in these inventions is used to produce backwards movement of molars and adjacent teeth when desired and stabilization of the molars against forward movement when they are being used as anchoring points in certain orthodontic procedures. The unyielding, tissue-covered basal bony areas behind the upper and lower front teeth are employed as stable anchoring regions; this is done by means of a semi-rigid pad whose soft, custom molded tissue surface is held in place against the anterior basal bony area in the maxilla or mandible.

A continuing problem has been the retention of the pad in place. A remedy adopted in the invention described in my U.S. Pat. No. 4,713,000 was the use of metal plates firmly attached to forward teeth to hold the appliance in the mouth. This has resulted in a more complex system with increased installation time.

A second continuing problem has been the difficulty of adjustment and increasing of pressure. This has been caused by the use of turning capstans (see 15 and 15' in FIG. 3 of U.S. Pat. No. 4,571,178). These devices require the inserting of a pin into a small opening, turning the capstan through approximately one quarter of a turn and then reinserting the pin into a succeeding small opening. The process is repeated on each side of the mouth until a proper adjustment is achieved.

It is an objective of the present invention to make the appliance retainable in the mouth but permitting easy removal when desired.

It is a second objective of the present invention to permit rapid pressure adjustment and to eliminate the use of turning capstans.

It is a third objective of the present invention to reduce the number of components in the appliance both for simplicity of use and economy of manufacture.

These and other objectives and the means used for their attainment will be apparent from the description of the invention presented below, and from the drawings.

DESCRIPTION OF THE DRAWINGS

The operation of the invention will be described by reference to FIGS. 1 and 2.

DESCRIPTION OF THE INVENTION

Figure 1:
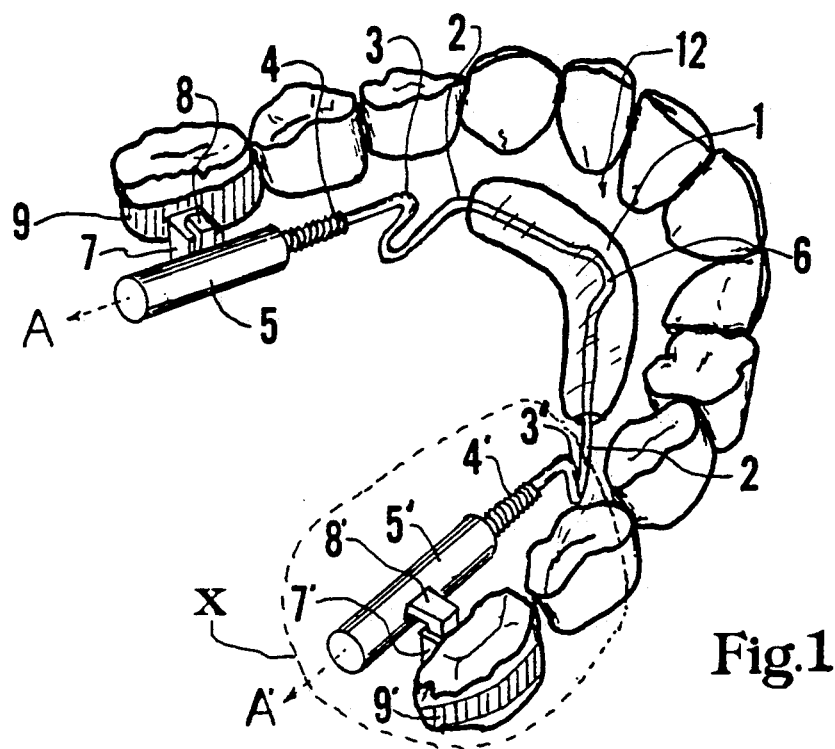
FIG. 1 is an isometric view of the appliance as it is positioned in the lower jaw oral cavity.
Figure 2:
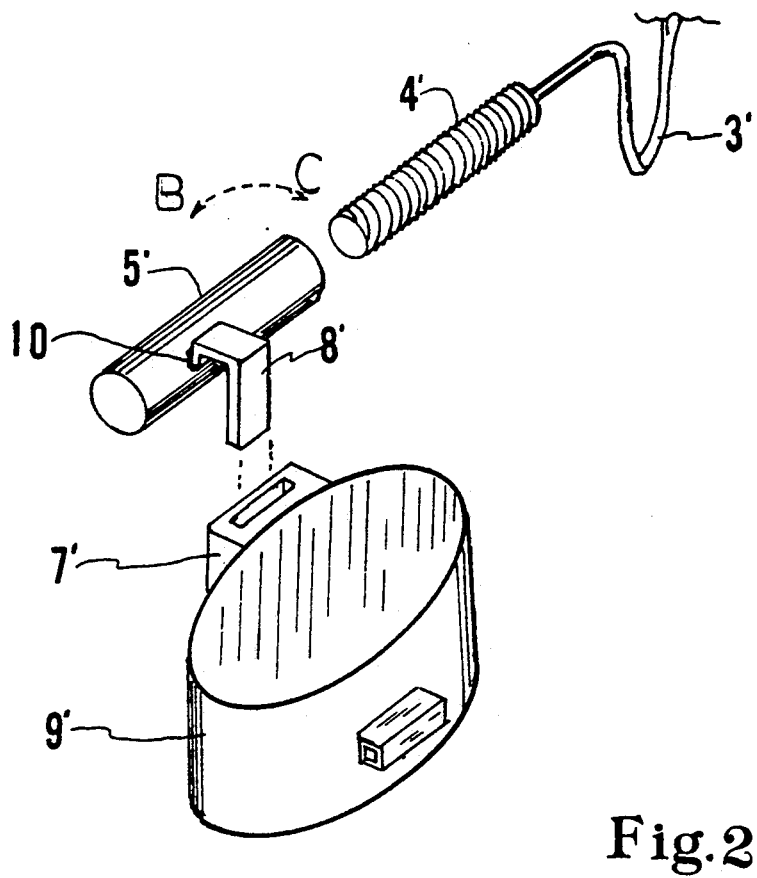
FIG. 2 is an isometric, expanded view of the portion X of FIG. 1 showing in detail the pressure applying system and the simplified mounting.

Forward anchoring of the appliance is accomplished with a semi-rigid pad 1 as shown in FIG. 1. The pad rests on tissue-covered anterior basal bony area 12 either in the maxilla or mandible. Undulation 6 is formed in the wire 2; this serves as a base for pad 1 and prevents the latter from twisting as a result of its contact with mouth tissue. The ends of wire 2 are coiled into the vertically oriented springs 3 and 3' and are rigidly joined to the externally threaded plungers 4 and 4' (FIGS. 1 and 2). The internally threaded cylinders 5 and 5' are provided with the rectangular inserts 8 and 8' which are rigidly joined to the cylinders. Inserts 8 and 8' fit into the receptacles 7 and 7' which are welded to the orthodontic bands 9 and 9'. The receptacles may be directly cemented to the molars in some cases. The bands 9 and 9' are cemented to the molars in normal orthodontic practice. Plungers 4 and 4' are initially fully threaded into closed cylinders 5 and 5'. The ends of the plungers preferably are fully threaded into the cylinders at the start of treatment because this gives a maximum adjustment range. To complete the installation the orthodontist slips the inserts 8 and 8' into the receptacles 7 and 7'. Springs 3 and 3' then exert force on pad 1 which results in reactive forces A and A' (FIG. 1) on the molars to which the appliance is attached. To increase or decrease the forces it is only necessary to remove inserts 8 and 8' from their receptacles, turn cylinders 5 and 5' in direction B or C for an integral number of turns and then reinstall the inserts. The configuration and orientation of the wire and springs 3 and 3' aids in retaining pad 1 in position without the use of auxiliary restraints as in my previous invention. The length of wire 2 and the size and shape of springs 3 and 3' can be customized for each particular case.

The appliance can be used to move rear molars posteriorly to help alleviate crowding in the dental arch and correct protrusions or may be combined with extraction of certain teeth when appropriate or necessary. When a rear molar is used as an anchoring point in normal orthodontic procedure, the appliance can be used to stabilize the molars, thus preventing their forward movement.

I claim:

1. A dental appliance for use as a molar movement inducer, inhibitor and controller comprised of:
   a. A semi-rigid pad with a soft tissue contacting lower surface to be held in place against a tissue covered basal, bony area posterial to the front teeth;
   b. A U-shaped wire embedded at its center in said semirigid pad and bent at each end into an S-shaped spring;
   c. An externally threaded plunger rigidly attached at each end of said S-shaped spring;
   d. A pair of hollow cylinders internally threaded and engaging said plungers, each cylinder provided with an insert to permit detachable joining to a receptacle attached to the lingual surface of said molar, whereby the hollow cylinders can be initially fully threaded onto said plungers, the pad placed against the applicable tissue covered basal bony area and each cylinder inserted into its corresponding receptacle, this attachment serving to produce a posterior force on each molar.

2. A dental appliance as described in claim 1 which can be adjusted to increase molar forces by removing each cylinder from its receptacle, turning the cylinder an integral number of turns with respect to its plunger and reinserting the cylinders into their receptacles.

* * * * *